(12) United States Patent
Levorse, Jr. et al.

(10) Patent No.: US 8,188,023 B2
(45) Date of Patent: *May 29, 2012

(54) 4-ALKYL CYCLOHEXANEPROPANAL COMPOUNDS AND THEIR USE IN PERFUME COMPOSITIONS

(75) Inventors: Anthony T. Levorse, Jr., Westfield, NJ (US); Robert P. Belko, Monroe, NJ (US); Benjamin Amorelli, Farmingdale, NJ (US); Michael G. Monteleone, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 283 days.

This patent is subject to a terminal disclaimer.

(21) Appl. No.: 12/619,325

(22) Filed: Nov. 16, 2009

(65) Prior Publication Data

US 2011/0117046 A1    May 19, 2011

(51) Int. Cl.
  *C11D 3/50* (2006.01)
  *A61Q 13/00* (2006.01)
(52) U.S. Cl. .............. 510/106; 568/420; 512/27; 512/8
(58) Field of Classification Search .............. 512/1, 27, 512/8; 510/106; 568/420
See application file for complete search history.

(56) References Cited

U.S. PATENT DOCUMENTS 7,226,644 B2    6/2007   Matsumoto et al.
7,834,219 B1*  11/2010   Levorse et al. ................ 568/420

FOREIGN PATENT DOCUMENTS

JP    3673873 B2    7/2005

OTHER PUBLICATIONS

Pabiot, J.M. et al. "Radical Addition of Hydrobromic Acid to Cyclanic Allylic Compounds in the Presence of Di-tert-butyl Peroxide. Substitution Reactions on Bromide." Lab. Chim. Org. Appl., Ec. Natl. Super. Chim., Paris, Fr. Comptes Rendus des Seances de l'Academic des Sciences, Serie C: Sciences Chimiques (1979) 273(6): 475-477.
English Abstract for the PABIOT, J.M. et al. reference.
Ohloff, G. et al. "Conformationally Controlled Odor Perception in 'Steroid-type' Scent Molecules." Helvetica Chimica Acta (1983) 66(5): 1343-1354.
Ishikawa, Y.et al. "Molecular Orbital Approach to Odor Molecules: Normal Fatty Acids and Cyclamenaldehydes." Int. J. Quantum Chem. (2000) 79(2): 101-108.

* cited by examiner

*Primary Examiner* — Douglas McGinty
(74) *Attorney, Agent, or Firm* — Elizabeth M. Quirk; XuFan Tseng; Joseph F. Leightner

(57) ABSTRACT

The present invention is directed to novel 4-alkyl cyclohexanepropanal compounds and a method of improving, enhancing or modifying a fragrance formulation through the addition of an olfactory acceptable amount of the novel compounds.

15 Claims, No Drawings

4-ALKYL CYCLOHEXANEPROPANAL COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances. For example, benzene compounds that differ slightly in substituents possess completely different odor profiles [Ishikawa, et al., International Journal of Quantum Chemistry 79: 101-108 (2000)]. In the case of tert-butyl cyclohexanes, the odor is said to be dependent on the compounds' conformation and therefore analogs adopting same conformation possess similar odor. Accordingly, many trans-compounds are shown to share pronounced urine-perspiration-type odor, while the corresponding cis-compounds are odorless or at the most possess weak and undefinable flowery or woody odor. However, some other trans- and cis-tert-butyl cyclohexanes are shown to possess opposite sensory activities [Ohloff, et al., Helvetica Chimica Acta 66, Fasc. 5: 1343-1354 (1983)]. Thus, it is hard for those with skill in the art to predict a given structure would be effective in sensory activities. Identifying desirable fragrance chemicals continues to pose difficult challenges.

SUMMARY OF THE INVENTION

The present invention provides novel chemicals and their unexpected advantageous use in enhancing, improving or modifying the fragrance of perfumes, colognes, toilet waters, personal products and the like.

More specifically, the present invention is directed to novel 4-alkyl cyclohexanepropanal compounds that exhibit unexpected strong fragrance effect and a method of improving, enhancing or modifying a fragrance formulation through the addition of an olfactory acceptable amount of 4-alkyl cyclohexanepropanals represented by Formula I set forth below:

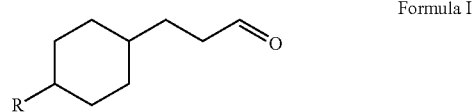

Formula I wherein R is selected from the group consisting of methyl, ethyl, propyl, isopropyl, butyl, isobutyl, and sec-butyl.

These and other embodiments of the present invention will be apparent by reading the following specification.

DETAILED DESCRIPTION OF THE INVENTION

It is known to those with the skill in the art that Formula I as defined above provides the following novel compounds:

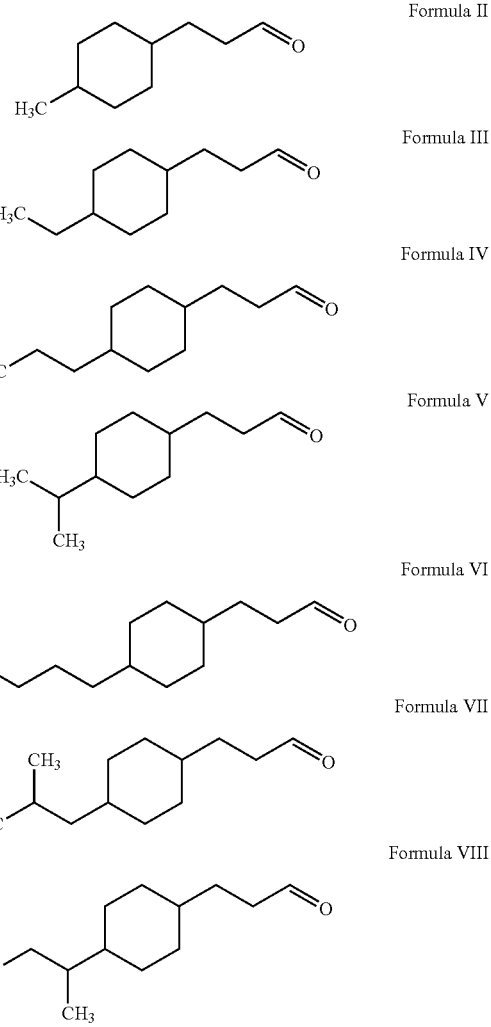

Those with the skill in the art will recognize that:

Formula II represents 4-methyl cyclohexanepropanal;

Formula III represents 4-ethyl cyclohexanepropanal;

Formula IV represents 4-propyl cyclohexanepropanal;

Formula V represents 4-isopropyl cyclohexanepropanal;

Formula VI represents 4-butyl cyclohexanepropanal;

Formula VII represents 4-isobutyl cyclohexanepropanal; and

Formula VIII represents 4-sec-butyl cyclohexanepropanal.

The compounds of the present invention can be prepared from 3-(4-alkyl-phenyl)-propionaldehydes, which are first synthesized via the Hoaglin-Hirsch reaction using corresponding 4-alkyl benzaldehydes (commercially available from Mitsubishi Gas Chemical America, Inc.). The reaction steps can be depicted by general Schemes 1 and 2 shown as follows:

Scheme 1. Preparation of 3-(4-alkyl-phenyl)-propionaldehydes.

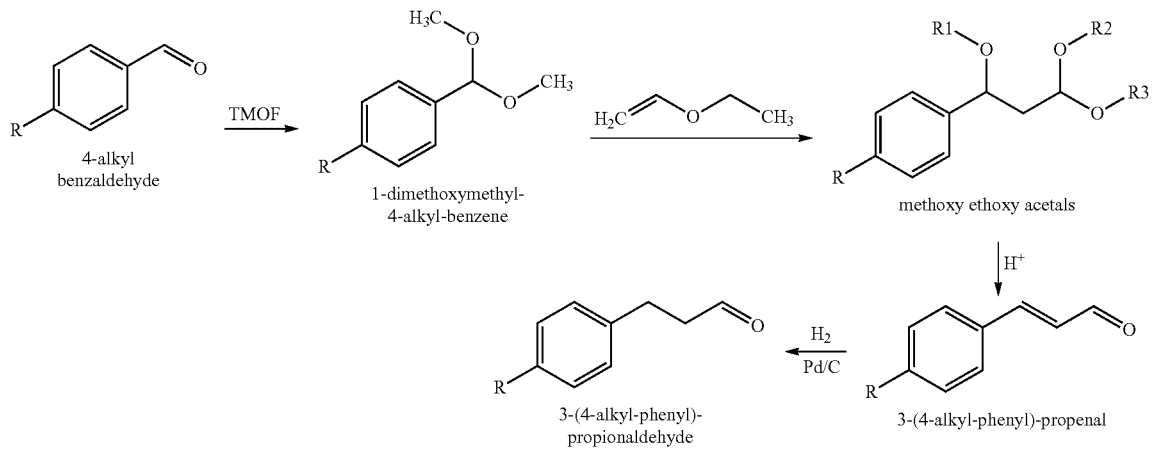

Scheme 2. Preparation of target compounds, 4-alkyl cyclohexanepropanals.

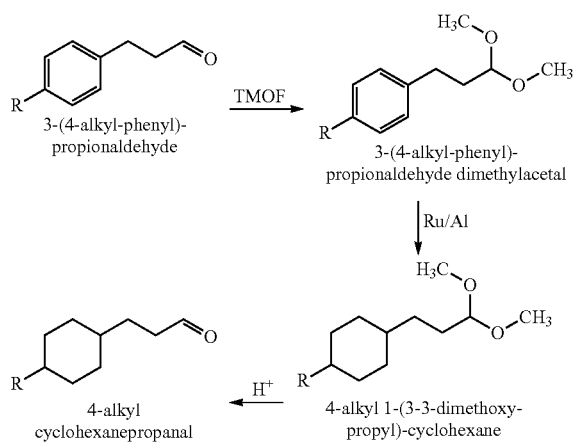

wherein R is defined as above;
$R_1$, $R_2$, and $R_3$ represent independently methyl or ethyl;
TMOF represents trimethyl orthoformate;
Pd/C represents palladium carbon catalyst; and
Ru/Al represents ruthenium on alumina catalyst.

Those with skill in the art will recognize that the 1,4-substituted aromatic rings contained in the compounds of the present invention give rise to a number of trans- and cis-isomers. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory acceptable amount is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 10 weight percent, more preferably from about 0.5 to about 8 weight percent, and even more preferably from about 1 to about 7 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation, the compounds of the present invention provide unexpected strong floral, muguet, and green characteristics and make the fragrance formulation more desirable and noticeable. The odor qualities found in the compounds of the present invention assist in beautifying and enhancing the finished accord and improve the performance of other materials in the fragrance formulation.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, Kg is understood to be kilogram, g is understood to be gram, and mmHg be millimeters (mm) of mercury (Hg). IFF as used in the examples is understood to mean International Flavors & Fragrances Inc., New York, N.Y., USA.

Example I mediate product 1-dimethoxymethyl-4-propyl-benzene (1.388 Kg) was obtained and charged to a second reaction flask at 25° C. Boron trifluride etherate (1 g, commercially available from Sigma-Aldrich, Inc.) was added. Ethyl vinyl ether (684 g, commercially available from Sigma-Aldrich, Inc.) was then fed for over 4 hours with the temperature maintained at 25-30° C. The reaction mass was quenched with saturated sodium carbonate (500 mL). The crude intermediate products methoxy ethoxy acetals were obtained, which were contained in the organic layer and confirmed by NMR analysis. Crude methoxy ethoxy acetals were hydrolyzed in the presence of water (500 mL) containing hydrochloric acid (37%, 50 g) at 90° C. for 5 hours and further catalytically hydrogenated in 2-propanol (200 mL) using palladium on carbon (5%, 1 g) and hydrogen in a 1 L zipper autoclave to provide the product 3-(4-propyl-phenyl)-propionaldehyde (1.008 Kg), which had a boiling point of 115° C. at a pressure of 6 mmHg.

The NMR analysis of the intermediate products methoxy ethoxy acetals was the following:

$^1$HNMR: 0.94 ppm (t, 3H, J=7.02 Hz), 1.13-1.27 ppm (m, 9H), 1.529-1.68 ppm (m, 2H), 1.84-1.91 ppm (m, 1H), 2.06-2.14 ppm (m, 1H), 2.55-2.59 ppm (m, 2H), 2.66 ppm (t, 2H, J=7.59 Hz), 3.17 ppm (s, 3H), 3.30 ppm (s, 3H), 3.33 ppm (s, 3H), 3.35-3.67 ppm (m, 6H), 4.19-4.60 ppm (m, 2H), 7.15 ppm (d, 2H, J=5.94 Hz), 7.21 ppm (d, 2H, J=7.33 Hz), 7.32 ppm (d, 2H, J=7.85 Hz), 7.78 ppm (d, 2H, J=7.94 Hz), 9.95 ppm (s, 1H).

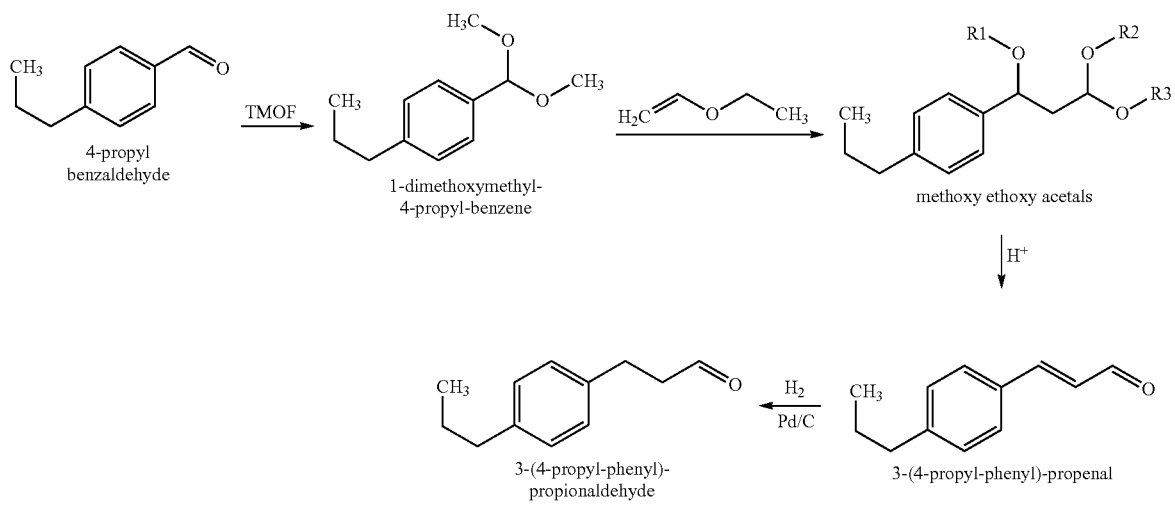

Preparation of 3-(4-propyl-phenyl)-propionaldehyde: A reaction flask was charged with 4-propyl benzaldehyde (1.064 Kg, commercially available from Mitsubishi Gas Chemical America, Inc.), methanol (500 mL), and trimethyl orthoformate (TMOF) (1.144 Kg, commercially available from Sigma-Aldrich, Inc.). The reaction mass was cooled to −10 to 0° C. and hydrochloric acid (37%, 1 g) was added in one portion. The reaction was instantaneous and the temperature was allowed to rise to 25° C. for over 30 minutes. The reaction mass was then quenched with sodium acetate (20 g) and the solvent was removed by evaporation. The crude inter- The NMR analysis of 3-(4-propyl-phenyl)-propionaldehyde was the following:

$^1$HNMR: 0.93 ppm (t, 3H, J=7.34 Hz), 1.62 ppm (m, 2H, J=7.52 Hz), 2.55 ppm (t, 2H, J=7.66 Hz), 2.75 ppm (t, 2H, J=7.56 Hz), 2.92 ppm (t, 2H, J=7.56 Hz), 7.10 ppm (s, 4H), 9.81 ppm (s, 1H)

The compound 3-(4-propyl-phenyl)-propionaldehyde was described as having floral, muguet, and green notes.

Example II

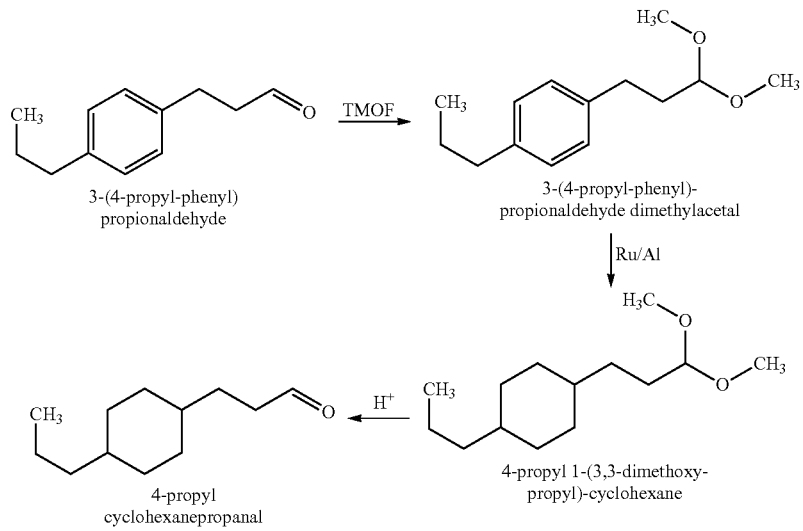

Preparation of 4-propyl cyclohexanepropanal (Formula IV): A reaction flask was charged with 3-(4-propyl-phenyl)-propionaldehyde (240 g, prepared as above), methanol (200 mL), and TMOF (150 g). The reaction mass was cooled to 0° C. and hydrochloric acid (37%, 1 g) was added in one portion. The reaction was exothermic and the temperature rose to 23° C. The reaction mass was quenched with sodium methoxide in methanol (25%, 10 g) and the solvent was removed by evaporation. The crude intermediate product 3-(4-propyl-phenyl)-propionaldehyde dimethylacetal (300 g), 2-propanol (100 mL), and rutheniium on alumina (3 g) were then charged to a 1 L zipper autoclave. The autoclave was purged with nitrogen followed by hydrogen. The autoclave was pressurized with 500 psi hydrogen and heated to 150° C. for 6 hours. The autoclave vessel was then cooled to an ambient temperature, depressurized, and purged with nitrogen. The reaction mass was filtered through celite to remove the catalyst and further hydrolyzed in the presence of water (2 L) containing hydrochloric acid (37%, 2 g) at 90° C. for 5 hours. The organic layer was separated and washed with saturated sodium carbonate solution (500 mL). Subsequent fractional distillation afforded 4-propyl cyclohexanepropanal (188 g), which had a boiling point of 107° C. at a pressure of 7 mmHg

$^1$HNMR: 0.85-0.95 ppm (m, 4H), 1.13-1.56 ppm (m, 11H), 1.60 ppm (q, 2H, J=7.24 Hz), 1.72-1.75 ppm (m, 2H), 2.29-2.35 ppm (m, 2H), 9.74-9.76 ppm (m, 1H)

The compound 4-propyl cyclohexanepropanal was described as having strong floral, muguet, and green notes.

Example III

Preparation of 4-methyl cyclohexanepropanal (Formula II): 4-Methyl cyclohexanepropanal was similarly prepared as described in Examples I and II. First, 4-methyl benzaldehyde (140 g, commercially available from Mitsubishi Gas Chemical America, Inc.) was used to obtain 3-(4-methyl-phenyl)-propionaldehyde (130 g) with a boiling point of 120° C. at a pressure of 21 mmHg 3-(4-Methyl-phenyl)-propionaldehyde (180 g) was consequently used to provide 4-methyl cyclohexanepropanal (104 g) with a boiling point of 112° C. at a pressure of 24 mmHg

$^1$HNMR: 0.85-0.97 ppm (m, 5H), 1.13-1.73 ppm (m, 10H), 2.40-2.45 ppm (m, 2H), 9.76-9.77 ppm (2 s, 1H)

The compound 4-methyl cyclohexanepropanal was described as having strong floral, muguet, and green notes.

Example IV

Preparation of 4-ethyl cyclohexanepropanal (Formula III): 4-Ethyl cyclohexanepropanal was similarly prepared as described in Examples I and II. First, 4-ethyl benzaldehyde (925 g, commercially available from Mitsubishi Gas Chemical America, Inc.) was used to obtain 3-(4-ethyl-phenyl)-propionaldehyde (878 g) with a boiling point of 129° C. at a pressure of 12 mmHg 3-(4-Ethyl-phenyl)-propionaldehyde (350 g) was consequently used to provide 4-ethyl cyclohexanepropanal (201 g) with a boiling point of 85° C. at a pressure of 3 mmHg

$^1$HNMR: 0.81-0.95 ppm (m, 5H), 1.05-1.77 ppm (m, 12H), 2.39-2.45 ppm (m, 2H), 9.76-9.77 ppm (2 s, 1H)

The compound 4-ethyl cyclohexanepropanal was described as having strong floral, muguet, and green notes.

Example V

Preparation of 4-isobutyl cyclohexanepropanal (Formula VII): 4-Isobutyl cyclohexanepropanal was similarly prepared as described in Examples I and II. First, 4-isobutyl benzaldehyde (600 g, commercially available from Mitsubishi Gas Chemical America, Inc.) was used to obtain 3-(4-isobutyl-phenyl)-propionaldehyde (568 g) with a boiling point of 119° C. at a pressure of 5 mmHg 3-(4-Isobutyl-phenyl)-propionaldehyde (400 g) was consequently used to provide 4-isobutyl cyclohexanepropanal (245 g) with a boiling point of 107° C. at a pressure of 4.4 mmHg

$^1$HNMR: 0.80-0.96 ppm (m, 8H), 1.02 ppm (t, ~33% of 2H, J=7.05 Hz), 1.12 ppm (t, ~67% of 2H, J=7.14 Hz), 1.24-1.35 ppm (m, 4H), 1.43-1.74 ppm (m, 7H), 2.42 ppm (q, 2H, J=7.67 Hz), 9.75-9.77 ppm (m, 1H)

The compound 4-isobutyl cyclohexanepropanal was described as having strong floral, muguet, and green notes.

Example VI

The fragrance formula exemplified as follows demonstrates that a 4-alkyl cyclohexanepropanal compound imparts muguet and green characters to a musk fragrance formula.

| Ingredients | Parts* + | Parts* − |
|---|---|---|
| Allyl Caproate | 10 | 10 |
| Leaf Alcohol | 5 | 5 |
| Kharismal ® | 15 | 15 |
| Seveniff ® | 100 | 100 |
| Alpha Damascone | 5 | 5 |
| Cashmeran ® | 10 | 10 |
| Nebulone ® | 50 | 50 |
| Iso E Super ® | 100 | 100 |
| Phenoxanol ® | 65 | 65 |
| Vivaldie ® | 20 | 20 |
| Verdox ® | 70 | 70 |
| Undecavertol | 5 | 5 |
| Applelide ® | 40 | 40 |
| 4-Propyl cyclohexanepropanal (Formula IV) | 45 | — |
| DPG | — | 45 |
| Total | 540 | 540 |

*"+" represents a 4-alkyl cyclohexanepropanal compound containing formula; and "−" represents a 4-alkyl cyclohexanepropanal compound non-containing formula.

Example VII

The fragrance formula exemplified as follows demonstrates that a 4-alkyl cyclohexanepropanal compound imparts muguet and green characters to a female fragrance formula.

| Ingredients | Parts* + | Parts* − |
|---|---|---|
| Salicynalva ® | 80 | 80 |
| Delta Damascone | 25 | 25 |
| Gamma Decalactone | 2 | 2 |
| Dimethyloctenol | 10 | 10 |
| Phenyl ethyl alcohol | 20 | 20 |
| Montaverdi ® | 5 | 5 |
| Geraniol | 150 | 150 |
| Linalool | 50 | 50 |
| Iso E Super ® | 123 | 123 |
| Cashmeran ® | 25 | 25 |
| Applelide ® | 100 | 100 |
| Galbascone ® | 15 | 15 |
| Leaf Alcohol | 5 | 5 |
| Globanone ® | 20 | 20 |
| Aldehyde C10 | 30 | 30 |
| Kharismal ® | 25 | 25 |
| Vanillin | 5 | 5 |
| 4-Propyl cyclohexanepropanal (Formula IV) | 10 | — |
| DPG | — | 10 |
| Total | 700 | 700 |

*"+" represents a 4-alkyl cyclohexanepropanal compound containing formula; and "−" represents a 4-alkyl cyclohexanepropanal compound non-containing formula.

What is claimed is:

1. A method of improving, enhancing or modifying a fragrance formulation through the addition of an olfactory acceptable amount of a compound:

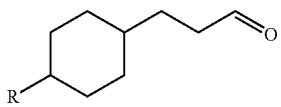

wherein R is selected from the group consisting of methyl, ethyl, propyl, isopropyl, butyl, isobutyl, and sec-butyl.

2. The method of claim 1, wherein the compound is 4-methyl cyclohexanepropanal.

3. The method of claim 1, wherein the compound is 4-ethyl cyclohexanepropanal.

4. The method of claim 1, wherein the compound is 4-propyl cyclohexanepropanal.

5. The method of claim 1, wherein the compound is 4-isopropyl cyclohexanepropanal.

6. The method of claim 1, wherein the compound is 4-butyl cyclohexanepropanal.

7. The method of claim 1, wherein the compound is 4-isobutyl cyclohexanepropanal.

8. The method of claim 1, wherein the compound is 4-sec-butyl cyclohexanepropanal.

9. The method of claim 1, wherein the fragrance formulation is incorporated into a product selected from the group consisting of a perfume, a cologne, a toilet water, a cosmetic product, a personal care product, a fabric care product, a cleaning product, and an air freshener.

10. The method of claim 9, wherein the cleaning product is selected from the group consisting of a detergent, a dishwashing composition, a scrubbing compound, and a window cleaner.

11. The method of claim 1, wherein the olfactory acceptable amount is from about 0.005 to about 10 weight percent of the fragrance formulation.

12. The method of claim 1, wherein the olfactory acceptable amount is from about 0.5 to about 8 weight percent of the fragrance formulation.

13. The method of claim 1, wherein the olfactory acceptable amount is from about 1 to about 7 weight percent of the fragrance formulation.

14. A fragrance formulation containing an olfactory effective amount of a compound:

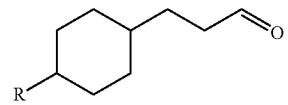

wherein R is selected from the group consisting of methyl, ethyl, propyl, isopropyl, butyl, isobutyl, and sec-butyl.

15. A fragrance product containing an olfactory effective amount of the compound:

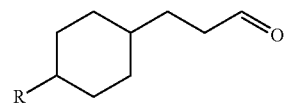

wherein R is selected from the group consisting of methyl, ethyl, propyl, isopropyl, butyl, isobutyl, and sec-butyl.

* * * * *